United States Patent
Ito et al.

(10) Patent No.: US 10,196,352 B2
(45) Date of Patent: Feb. 5, 2019

(54) METHOD FOR PRODUCING EPSILON-CAPROLACTAM

(71) Applicant: TORAY INDUSTRIES, INC., Tokyo (JP)

(72) Inventors: Masateru Ito, Kamakura (JP); Daijiro Tsukamoto, Kamakura (JP); Kenji Kawamura, Kamakura (JP); Kohei Yamashita, Nagoya (JP); Masato Akahira, Nagoya (JP); Katsushige Yamada, Kamakura (JP); Koji Yamauchi, Nagoya (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

(21) Appl. No.: 15/523,120

(22) PCT Filed: Oct. 27, 2015

(86) PCT No.: PCT/JP2015/080183
§ 371 (c)(1),
(2) Date: Apr. 28, 2017

(87) PCT Pub. No.: WO2016/068108
PCT Pub. Date: May 6, 2016

(65) Prior Publication Data
US 2017/0320819 A1 Nov. 9, 2017

(30) Foreign Application Priority Data

Oct. 30, 2014 (JP) .................................. 2014-221658
Oct. 30, 2014 (JP) .................................. 2014-221659
Jun. 5, 2015 (JP) .................................. 2015-114451

(51) Int. Cl.
| | |
|---|---|
| *C07D 201/08* | (2006.01) |
| *C07D 223/10* | (2006.01) |
| *B01J 23/44* | (2006.01) |
| *C08G 69/14* | (2006.01) |
| *C07B 61/00* | (2006.01) |

(52) U.S. Cl.
CPC ............ *C07D 201/08* (2013.01); *B01J 23/44* (2013.01); *C07D 223/10* (2013.01); *C08G 69/14* (2013.01); *C07B 61/00* (2013.01); *Y02P 20/52* (2015.11)

(58) Field of Classification Search
CPC .................................................... C07D 201/08
See application file for complete search history.

(56) References Cited

U.S. PATENT DOCUMENTS

2007/0244317 A1* 10/2007 Crabtree ............ C07D 207/267
540/484

FOREIGN PATENT DOCUMENTS

| JP | 53-68768 A | 6/1978 | | |
|---|---|---|---|---|
| JP | 57-88148 A | 6/1982 | | |
| JP | 2007-509914 A | 4/2007 | | |
| JP | 2012-515795 A | 7/2012 | | |
| WO | WO 2010/085712 A2 | 7/2010 | | |
| WO | WO 2012/141997 A1 | 10/2012 | | |
| WO | WO2012141997 | * 10/2012 | ........... | C07D 223/10 |
| WO | WO 2013/126250 A1 | 8/2013 | | |
| WO | WO2013126250 | * 8/2013 | ........... | C07D 223/10 |

OTHER PUBLICATIONS

International Search Report, issued in PCT/JP2015/080183, PCT/ISA/210, dated Jan. 19, 2016.
Written Opinion of the International Searching Authority, issued in PCT/JP2015/080183, PCT/ISA/237, dated Jan. 19, 2016.
Extended European Search Report dated Mar. 9, 2018, in European Patent Application No. 15854971.7.

* cited by examiner

*Primary Examiner* — Paul V Ward
(74) *Attorney, Agent, or Firm* — Birch, Stewart, Kolasch & Birch, LLP

(57) ABSTRACT

A method for selective production of ε-caprolactam, wherein a substance inducible from a biomass resource is used as a material; the reaction process is short; ammonium sulfate is not produced as a by-product; and production of by-products is suppressed; is disclosed. The method for producing ε-caprolactam comprises the step of reacting a particular compound inducible from a biomass resource, such as α-hydromuconic acid, 3-hydroxyadipic acid, or 3-hydroxyadipic acid-3,6-lactone, or a salt thereof with hydrogen or ammonia.

14 Claims, No Drawings

METHOD FOR PRODUCING EPSILON-CAPROLACTAM

TECHNICAL FIELD

The present invention relates to a method for producing ε-caprolactam, which can be used as a material of polyamide.

BACKGROUND ART

ε-Caprolactam is an important chemical material that can be used as a material for nylons and the like, and is industrially produced worldwide. It is mostly used as a material for Nylon 6, which is a polyamide.

As an industrial production method for ε-caprolactam, a production method using the Beckmann rearrangement reaction with fuming sulfuric acid from cyclohexanone oxime has been widely employed. However, there is a problem that a large amount of ammonium sulfate is produced as a by-product in the neutralization step in the Beckmann rearrangement reaction. On the other hand, as production methods for ε-caprolactam that do not produce ammonium sulfate as a by-product, a method in which combination of ammoximation and the gas-phase Beckmann rearrangement reaction is used from cyclohexanone (Non-patent Document 1) and a method in which ε-caprolactam is brought into contact with a catalyst in the presence of ammonia (Patent Document 1) have been proposed.

All of the above production methods for ε-caprolactam use crude oil as the original material. From the viewpoint of possible depletion of oil resources in the future, and the problem of global warming due to emission of greenhouse gases by mining and use of fossil resources, development of methods for producing caprolactam using alternative materials is necessary. In particular, development of a method for producing caprolactam from biomass, which is a regenerative resource, or from substances inducible from biomass resources, has been demanded.

Several methods for producing ε-caprolactam from substances inducible from biomass resources have been reported so far. For example, Patent Document 2 discloses a method for producing ε-caprolactam through ε-caprolactone using 5-hydroxymethylfurfural as a material. Patent Document 3 discloses a method for producing ε-caprolactam by using adipic acid as a material and reacting it with hydrogen and ammonia. Patent Document 4 discloses a method for producing ε-caprolactam by using muconic acid as a material and reacting it with hydrogen and ammonia.

PRIOR ART DOCUMENTS

Patent Documents

[Patent Document 1] JP 4164603 B
[Patent Document 2] WO 2011/149339
[Patent Document 3] WO 2013/126250
[Patent Document 4] WO 2012/141997

Non-Patent Documents

[Non-patent Document 1] Applied Catalysis A: General, vol. 221, 359-366 (2001)

SUMMARY OF THE INVENTION

Problems to be Solved by the Invention

The method of Patent Document 2 is a method in which a plurality of stages of reaction process including hydrogenation of 5-hydroxydimethylfurfural, hydrogenolysis of 2,5-dimethylhydroxymethyltetrahydrofuran, intramolecular dehydration condensation of 1,2,6-hexanediol, hydrogenation ring-opening of (tetrahydro-2H-pyran-2-yl) methanol, intramolecular ring closure of 1,6-hexanediol, and amidation of ε-caprolactone are carried out to synthesize ε-caprolactam, which is not preferred from an industrial point of view.

In the method of Patent Document 3, ε-caprolactam can be synthesized by a single-step reaction process using as a material adipic acid, which is inducible from biomass resources. However, the yield of ε-caprolactam is low, and by-products such as hexamethyleneimine and 6-aminocaproic acid are produced, which is problematic.

In the method of Patent Document 4, ε-caprolactam can be synthesized by a single-step reaction process using as a material muconic acid, which is inducible from biomass resources. Similarly to the method disclosed in Patent Document 3, however, the yield of ε-caprolactam is low, and by-products such as hexamethyleneimine and hexanamide are produced, which is problematic. Further, muconic acid includes three geometric isomers (cis-cis isomer, trans-trans isomer, and cis-trans isomer) depending on its two double bonds, and these isomers have different reactivities. Thus, for synthesizing ε-caprolactam with high yield, muconic acid needs to be isomerized in advance to the trans-trans isomer, which has high reactivity.

An object of the present invention is to provide a method for selective production of ε-caprolactam, wherein a substance inducible from a biomass resource is used as a material; the reaction process is short; ammonium sulfate is not produced as a by-product; and production of by-products is suppressed.

Means for Solving the Problems

The present inventors intensively studied to solve the problems described above, and, as a result, discovered a method for producing ε-caprolactam in which a compound represented by General Formula (I) or (II), which is a substance inducible from biomass resources, is used as a material, and the compound is reacted with hydrogen and ammonia, wherein ammonium sulfate is not produced as a by-product, and production of by-products is suppressed, thereby completing the present invention.

That is, the present invention is constituted by the following (1) to (10).

(1) A method for producing ε-caprolactam, comprising the step of reacting a compound represented by General Formula (I) or (II):

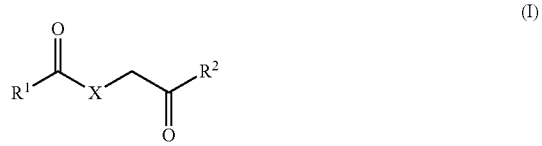

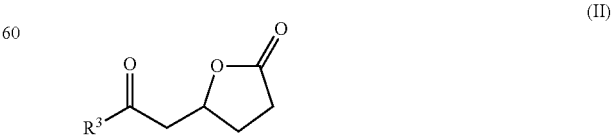

[wherein $R^1$, $R^2$, and $R^3$ each independently represent $OR^4$ or $NR^5R^6$; each $R^4$ independently represents H or $C_1$-$C_5$ alkyl; each $R^5$ independently represents H or $C_1$-$C_5$ alkyl; and X represents —CH(OH)CH$_2$CH$_2$—, CH$_2$CH(OH)CH$_2$—, or —CH$_2$CH=CH—]
or a salt thereof with hydrogen and ammonia.

(2) The method according to (1), wherein the compound represented by General Formula (I) or (II) is α-hydromuconic acid, 3-hydroxyadipic acid, or 3-hydroxyadipic acid-3,6-lactone, or a salt thereof.

(3) The method according to (2), wherein the compound represented by General Formula (I) or (II) is α-hydromuconic acid or a salt thereof.

(4) The method according to (2), wherein the compound represented by General Formula (I) or (II) is 3-hydroxyadipic acid or a salt thereof.

(5) The method according to (2), wherein the compound represented by General Formula (I) or (II) is 3-hydroxyadipic acid-3,6-lactone or a salt thereof.

(6) The method according to any one of (1) to (5), wherein the step is carried out in the presence of a catalyst.

(7) The method according to (6), wherein the catalyst is at least one selected from the group consisting of palladium, platinum, gold, copper, ruthenium, rhodium, cobalt, rhenium, and nickel.

(8) The method according to (7), wherein the catalyst is at least one selected from the group consisting of palladium, platinum, gold, ruthenium, rhodium, cobalt, rhenium, and nickel.

(9) The method according to (8), wherein the catalyst is palladium.

(10) The method according to any one of (1) to (9), wherein the hydrogen pressure at the beginning of the reaction in the step is 0.5 MPa to 10 MPa at normal temperature in terms of the gauge pressure.

Effect of the Invention

By the present invention, an ε-caprolactam can be obtained highly selectively while production of by-products can be suppressed.

MODE FOR CARRYING OUT THE INVENTION

The present invention is described below in more detail.

In the present invention, "biomass resources" means regenerative organic resources derived from organisms, which are resources comprising organic matters produced by carbon dioxide fixation using solar energy by plants. Specific examples of the biomass resources include maize, sugarcane, tubers, wheat, rice, soybean, pulp, kenaf, rice straw, wheat straw, bagasse, corn stover, switchgrass, weeds, waste paper, woods, charcoal, natural rubber, cotton, soybean oil, palm oil, safflower oil, and castor oil.

In the present invention, "substances inducible from biomass resources" means substances that are induced, that can be induced, or that were induced, from the biomass resources by fermentation, chemical conversion, or the like.

In the present invention, a compound represented by General Formula (I) or (II), or a salt thereof is used as a material.

In General Formula (I) or (II), $R^1$, $R^2$, and $R^3$ each independently represent $OR^4$ or $NR^5R^6$; each $R^4$ independently represents H, $C_1$-$C_5$ alkyl, alkali metal, or NH$_4$; each $R^5$ independently represents H or $C_1$-$C_5$ alkyl; and X represents —CH(OH)CH$_2$CH$_2$—, CH$_2$CH(OH)CH$_2$—, —CH=CHCH$_2$—, or —CH$_2$CH=CH—].

In the method of the present invention, among the compounds represented by General Formula (I) or (II), a single compound may be used as a material, or a mixture of a plurality of compounds may be used as a material.

In the compound represented by General Formula (I) or (II) used in the present invention, $R^1$, $R^2$, and $R^3$ are preferably $OR^4$ wherein $R^4$ is more preferably H or $C_1$-$C_5$ alkyl, especially preferably OH, OMe, or OEt.

More specifically, the compound represented by General Formula (I) or (II) used in the present invention is preferably a compound represented by any of the following Formulae (I-1) to (I-5), and Formulae (II-1) to (II-2). Among these, α-hydromuconic acid, which is represented by Formula (I-1), 3-hydroxyadipic acid, which is represented by Formula (I-2), or 3-hydroxyadipic acid-3,6-lactone, which is represented by Formula (II-1), is more preferred.

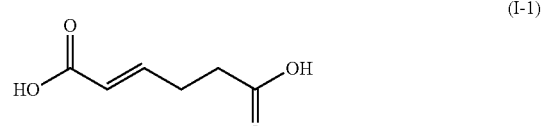

(I-1)

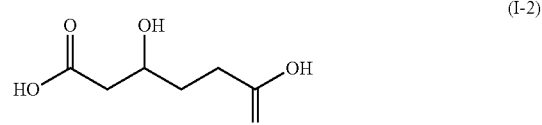

(I-2)

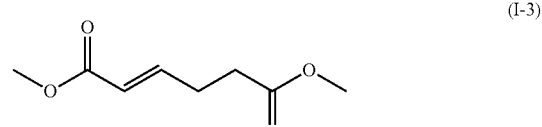

(I-3)

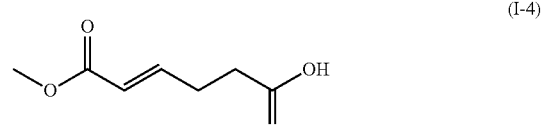

(I-4)

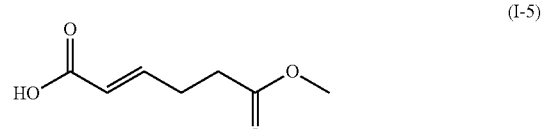

(I-5)

(II-1)

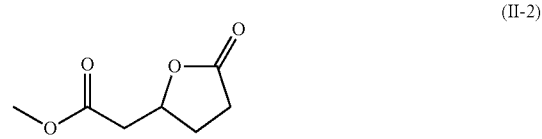

(II-2)

α-Hydromuconic acid, which is represented by Formula (I-1), is an organic compound also called 2-hexenedicarboxylic acid, which is a dicarboxylic acid having six carbon atoms in which a double bond is present at α-position of the carbonyl carbon. Since the double bond is present in the molecule, α-hydromuconic acid has a cis-isomer and a trans-isomer as geometric isomers. In the production method of the present invention, any of the cis-isomer, trans-isomer, and a mixture of the cis-isomer and the trans-isomer may be used as a material.

α-Hydromuconic acid (I-1) can be obtained by induction from biomass resources. For example, a naturally occurring microorganism such as a *Cupriavidus* microorganism, *Acinetobacter* microorganism, *Delftia* microorganism, *Shimwellia* microorganism, *Escherichia* microorganism, or *Pseudomonas* microorganism, or a microorganism artificially improved therefrom by genetic recombination or the like, having a capacity to produce α-hydromuconic acid may be used for fermentation production of α-hydromuconic acid using as a material a carbon source inducible from biomass resources, such as glucose, xylose, or glycerol. As described later, α-hydromuconic acid can be synthesized also by intramolecular dehydration of 3-hydroxyadipic acid, which can be induced from biomass resources.

3-Hydroxyadipic acid, which is represented by Formula (I-2), is an organic compound also called 3-hydroxyhexanedicarboxylic acid, which is a dicarboxylic acid having six carbon atoms in which a hydroxyl group is present at β-position of the carbonyl carbon.

3-Hydroxyadipic acid (I-2) can be obtained by induction from biomass resources. For example, a naturally occurring microorganism such as a *Cupriavidus* microorganism, *Acinetobacter* microorganism, *Delftia* microorganism, *Shimwellia* microorganism, *Escherichia* microorganism, or *Pseudomonas* microorganism, or a microorganism artificially improved therefrom by genetic recombination or the like, having a capacity to produce 3-hydroxyadipic acid may be used for fermentation production of 3-hydroxyadipic acid using as a material a carbon source inducible from biomass resources, such as glucose, xylose, or glycerol. As described later, 3-hydroxyadipic acid can be synthesized also by hydrogen reduction of β-ketoadipic acid, which can be induced from biomass resources.

3-Hydroxyadipic acid-3,6-lactone (II-1) can be obtained by induction from biomass resources. For example, as shown in Scheme 1, 3-hydroxyadipic acid-3,6-lactone can be induced from β-ketoadipic acid. β-Ketoadipic acid is a compound biosynthesized in the process of metabolism of an aromatic compound such as protocatechuic acid or catechol (β-ketoadipate pathway). For example, as a method for producing β-ketoadipic acid using this pathway, JP 2012-59 A discloses a method in which recombinant *Pseudomonas putida* is used for fermentation production of 0-ketoadipic acid from protocatechuic acid. Here, protocatechuic acid and catechol are biomass resource-derived substances that can be produced by microbial fermentation using sugars as carbon sources. For example, a method for fermentation production of protocatechuic acid and catechol using glucose as a single carbon source has been disclosed in U.S. Pat. No. 5,272,073 B. Thus, 3-hydroxyadipic acid-3,6-lactone can be said to be a substance inducible from biomass resources.

The method for producing ε-caprolactam of the present invention is characterized in that, among the compounds represented by General Formula (I) or General Formula (II), especially α-hydromuconic acid (I-1), 3-hydroxyadipic acid (I-2), 3-hydroxyadipic acid-3,6-lactone (II-1), or the like that is inducible from biomass resources can be used as a material. Of course, however, a compound represented by General Formula (I) or (II) derived from a fossil resource such as petroleum can also be used as a material.

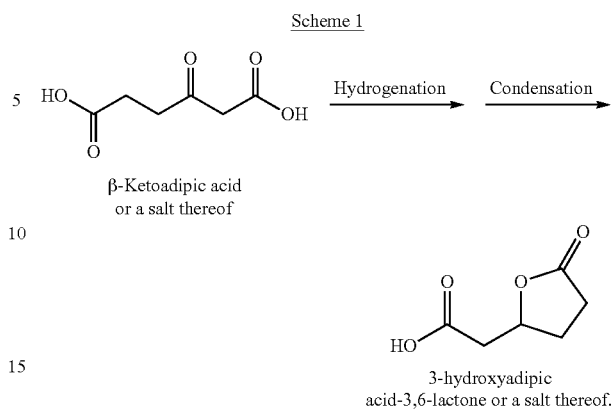

Scheme 1

β-Ketoadipic acid or a salt thereof 3-hydroxyadipic acid-3,6-lactone or a salt thereof.

The material used in the production method of the present invention may be either a free compound or a salt of a compound represented by General Formula (I) or (II). Alternatively, a mixture of a free compound and a salt may be used. The salt may be either a monovalent salt or a divalent salt. For example, an alkali metal salt, alkaline earth metal salt, or ammonium salt may be used.

More specifically, examples of the monovalent salt of the compound represented by General Formula (I) or (II) include monoammonium salt, monolithium salt, monosodium salt, and monopotassium salt of the compound, and examples of the divalent salt include diammonium salt, dilithium salt, disodium salt, dipotassium salt, magnesium salt, calcium salt, and diammonium salt of the compound. A mixture of different salts among these may also be used as the material.

[Catalyst]

In the method for producing ε-caprolactam of the present invention, the reaction can be promoted by performing the reaction in the presence of a catalyst. The catalyst is preferably a noble metal. Specific examples of the catalyst include palladium, platinum, gold, copper, ruthenium, rhodium, cobalt, rhenium, and nickel. The catalyst may also be an alloy containing one or more of these.

Although the noble metal may be used as it is, the noble metal may be supported on a carrier from the viewpoint of saving the amount of the noble metal used, or increasing the catalyst surface area. Examples of the carrier include oxides such as aluminium oxide (alumina), silicon dioxide, zeolite, titanium oxide, zirconium oxide, tungsten oxide, and chromium oxide; and composite oxides such as silica-alumina, silica-zirconia, silica-titania, silica-magnesia, alumina-zirconia, alumina-boria, tungsten-alumina, and tungsten-silica; and carbon. In cases where the noble metal is supported on the carrier, the amount of the noble metal supported is usually 0.1 to 10% by weight in terms of the element with respect to the carrier, although the amount may be appropriately selected depending on the compound represented by General Formula (I) or (II) or the salt thereof.

In cases where the reaction is carried out in the presence of a catalyst, the amount of the catalyst added may be 0.1 to 20% by weight with respect to the compound represented by General Formula (I) or (II) or the salt thereof, which is the reaction substrate. The catalyst may be repeatedly used after being separated by filtration following completion of the reaction. In cases where the catalyst is used repeatedly, it is more preferably used after being subjected to an activation treatment by heat treatment under an atmosphere of an inert gas such as nitrogen, helium, or argon, or under hydrogen atmosphere.

[Hydrogen, Ammonia]

The hydrogen and the ammonia in the present invention may be added at once (batch method), or may be added sequentially (continuous method) to the reaction container. The hydrogen and the ammonia may be individually added, or may be added as a mixture.

The hydrogen used may be a mixed gas with nitrogen, helium, argon, water vapor, and/or the like.

The pressure of the hydrogen is not limited. In cases where the pressure is too low, the reaction time is long, so that the pressure is preferably 0.5 MPa to 10 MPa (gauge pressure) at normal temperature at the beginning of the reaction.

The ammonia may be added to the reaction container in either a gas state or a liquid state. In cases where the ammonia is added in a liquid state, liquid ammonia or a solution in which ammonia is dissolved at normal pressure may be used. For example, aqueous ammonia solution, ammonia-dioxane solution, ammonia-chloroform solution, ammonia-ether solution, ammonia-alcohol solution, or the like may be preferably used.

The pressure in cases of use of ammonia gas is not limited. In cases where the pressure is too low, the reaction time is long, so that the pressure is preferably 0.1 MPa to 5 MPa (gauge pressure) at normal temperature at the beginning of the reaction.

[Solvent]

In the method for producing ε-caprolactam of the present invention, the reaction may be carried out in the presence of a solvent. The solvent used is not limited, and examples of the solvent include alcohol-based solvents such as methanol, ethanol, and butanol; halogen-based solvents such as carbon tetrachloride, dichloromethane, and chloroform; aliphatic hydrocarbon-based solvents such as pentane, hexane, heptane, octane, and decane; aromatic hydrocarbon-based solvents such as benzene, toluene, and xylene; ether-based solvents such as dimethylether, diethylether, 1,2-dimethoxyethane, diglyme, tetrahydrofuran, and dioxane; γ-butyrolactone; N-methylpyrrolidone; dimethylsulfoxide; and water. The solvent may also be a mixed solvent of two or more kinds of these. The solvent used is preferably an aprotic solvent such as dioxane, diglyme, or tetrahydrofuran.

3-Hydroxyadipic acid-3,6-lactone (II-1) can be easily dissolved in polar solvents such as alcohols, γ-butyrolactone, N-methylpyrrolidone, dimethylsulfoxide, and water; as well as in nonpolar-solvents such as 1,2-dimethoxyethane, diglyme, tetrahydrofuran, and dioxane, containing an oxygen atom. Thus, in cases where 3-hydroxyadipic acid-3,6-lactone is used as a material, use of these solvents allows feeding of the material at a high concentration, and the productivity of caprolactam, which is the substance of interest, can therefore be increased.

[Reaction Temperature]

In the method for producing ε-caprolactam of the present invention, the reaction may be carried out under heating conditions. The reaction temperature is preferably 100° C. to 350° C., more preferably 150° C. to 300° C. in terms of the internal temperature of the reaction container. The reaction time is appropriately selected depending on the reaction temperature and other conditions. The reaction time is usually about 0.5 hour to 12 hours.

[Recovery of ε-Caprolactam]

In the method for producing ε-caprolactam of the present invention, the ε-caprolactam can be recovered by an ordinary separation purification operation(s) such as filtration, extraction, and/or distillation after the completion of the reaction. The hydrogen and the ammonia may be recycled into the reaction system. In cases where an intermediate such as adipamide (hexanedioic acid amide) is produced besides ε-caprolactam, the yield of ε-caprolactam can be increased by its recovery and recycling.

[Polyamide Polymerization]

The ε-caprolactam obtained by the method for producing ε-caprolactam of the present invention can be used for production of a polyamide using it as a material. As a method for producing the polyamide, a known method in which ε-caprolactam is subjected to ring-opening polymerization may be applied (see Osamu Fukumoto ed., "Polyamide Resin Handbook", Nikkan Kogyo Shimbun, Ltd. (January, 1998)).

EXAMPLES

The present invention is described below in more detail by way of Examples. However, the present invention is not limited to the Examples below. In the Examples, the reaction results are defined according to the following equations.

Material conversion rate (%)=100×(supplied material (mol)−unreacted material (mol))÷supplied material (mol)

ε-Caprolactam yield (%)=100×yielded ε-caprolactam (mol)÷supplied material (mol)

Adipamide yield (%)=100×yielded adipamide (mol)÷supplied material (mol)

Hexamethyleneimine yield (%)=100×yielded hexamethyleneimine (mol)÷supplied material (mol)

Mole balance (%)=100×total reaction product (mol)÷supplied material (mol)

Reference Example 1 Preparation of α-Hydromuconic Acid (I-1)

The α-hydromuconic acid used in the present invention was prepared by chemical synthesis.

First, 1.5 L of super-dehydrated tetrahydrofuran (manufactured by Wako Pure Chemical Industries, Ltd.) was added to 13.2 g (0.1 mol) of succinic acid monomethyl ester (manufactured by Wako Pure Chemical Industries, Ltd.), and 16.2 g (0.1 mol) of carbonyldiimidazole (manufactured by Wako Pure Chemical Industries, Ltd.) was added thereto with stirring, followed by stirring the resulting mixture under nitrogen atmosphere for 1 hour at room temperature. To this suspension, 15.6 g (0.1 mol) of malonic acid monomethyl ester potassium salt and 9.5 g (0.1 mol) of magnesium chloride were added. The resulting mixture was stirred under nitrogen atmosphere for 1 hour at room temperature, and then stirred at 40° C. for 12 hours. After the reaction, 0.05 L of 1 mol/L hydrochloric acid was added to the mixture, and extraction with ethyl acetate was carried out. By separation purification by silica gel column chromatography (hexane:ethyl acetate=1:5), 13.1 g of pure 3-oxohexanedicarboxylic acid dimethyl ester was obtained. Yield: 70%.

To 10 g (0.05 mol) of the 3-oxohexanedicarboxylic acid dimethyl ester obtained, 0.1 L of methanol (manufactured by Kokusan Chemical Co., Ltd.) was added, and 2.0 g (0.05 mol) of sodium borohydride (manufactured by Wako Pure Chemical Industries, Ltd.) was added to the resulting mixture with stirring, followed by stirring the mixture at room temperature for 1 hour. Subsequently, 0.02 L of 5 mol/L aqueous sodium hydroxide solution was added thereto, and the resulting mixture was stirred at room temperature for 2 hours. After the reaction, the pH was adjusted to 1 with 5 mol/L hydrochloric acid, and the mixture was then concentrated using a rotary evaporator. By recrystallization with water, 7.2 g of pure α-hydromuconic acid was obtained. Yield: 95%.

$^1$H-NMR (400 MHz, CD$_3$OD): δ2.48 (m, 4H), δ5.84 (d, 1H), δ6.96 (m, 1H).

Reference Example 2 Preparation of 3-Hydroxyadipic (I-2) Acid

The 3-hydroxyadipic acid used in the present invention was prepared by chemical synthesis.

First, 1.5 L of super-dehydrated tetrahydrofuran (manufactured by Wako Pure Chemical Industries, Ltd.) was added to 13.2 g (0.1 mol) of succinic acid monomethyl ester (manufactured by Wako Pure Chemical Industries, Ltd.), and 16.2 g (0.1 mol) of carbonyldiimidazole (manufactured by Wako Pure Chemical Industries, Ltd.) was added thereto with stirring, followed by stirring the resulting mixture under nitrogen atmosphere for 1 hour at room temperature. To this suspension, 15.6 g (0.1 mol) of malonic acid monomethyl ester potassium salt and 9.5 g (0.1 mol) of magnesium chloride were added. The resulting mixture was stirred under nitrogen atmosphere for 1 hour at room temperature, and then stirred at 40° C. for 12 hours. After the reaction, 0.05 L of 1 mol/L hydrochloric acid was added to the mixture, and extraction with ethyl acetate was carried out. By separation purification by silica gel column chromatography (hexane:ethyl acetate=1:5), 13.1 g of pure 3-oxohexanedicarboxylic acid dimethyl ester was obtained. Yield: 70%.

To 10 g (0.05 mol) of the 3-oxohexanedicarboxylic acid dimethyl ester obtained, 0.1 L of methanol (manufactured by Kokusan Chemical Co., Ltd.) was added, and 0.02 L of 5 mol/L aqueous sodium hydroxide solution was added to the resulting mixture with stirring, followed by stirring the mixture at room temperature for 2 hours. After the reaction, the pH was adjusted to 1 with 5 mol/L hydrochloric acid. Subsequently, 2.0 g (0.05 mol) of sodium borohydride (manufactured by Wako Pure Chemical Industries, Ltd.) was added thereto, and the resulting mixture was stirred at room temperature for 2 hours. After the reaction, the mixture was concentrated using a rotary evaporator. By recrystallization with water, 7.2 g of pure 3-hydroxyadipic acid was obtained. Yield: 95%.

$^1$H-NMR (400 MHz, CD3OD): δ1.70 (m, 1H), δ1.83 (m, 1H), δ2.42 (m, 4H), 64.01 (m, 1H).

Reference Example 3 Preparation of 3-Hydroxyadipic Acid-3,6-Lactone (II-1)

The 3-hydroxyadipic acid-3,6-lactone used in the present invention was prepared by chemical synthesis.

First, 1.5 L of super-dehydrated tetrahydrofuran (manufactured by Wako Pure Chemical Industries, Ltd.) was added to 13.2 g (0.1 mol) of succinic acid monomethyl ester (manufactured by Wako Pure Chemical Industries, Ltd.), and 16.2 g (0.1 mol) of carbonyldiimidazole (manufactured by Wako Pure Chemical Industries, Ltd.) was added thereto with stirring, followed by stirring the resulting mixture under nitrogen atmosphere for 1 hour at room temperature. To this suspension, 15.6 g (0.1 mol) of malonic acid monomethyl ester potassium salt and 9.5 g (0.1 mol) of magnesium chloride were added. The resulting mixture was stirred under nitrogen atmosphere for 1 hour at room temperature, and then stirred at 40° C. for 12 hours. After the reaction, 0.05 L of 1 mol/L hydrochloric acid was added to the mixture, and extraction with ethyl acetate was carried out. By separation purification by silica gel column chromatography (hexane:ethyl acetate=1:5), 13.1 g of pure 3-oxohexanedicarboxylic acid dimethyl ester was obtained. Yield: 70%.

To 10 g (0.05 mol) of the 3-oxohexanedicarboxylic acid dimethyl ester obtained, 0.1 L of methanol (manufactured by Kokusan Chemical Co., Ltd.) was added, and 0.02 L of 5 mol/L aqueous sodium hydroxide solution was added to the resulting mixture with stirring, followed by stirring the mixture at room temperature for 2 hours. After the reaction, the pH was adjusted to 1 with 5 mol/L hydrochloric acid. Subsequently, 2.0 g (0.05 mol) of sodium borohydride (manufactured by Wako Pure Chemical Industries, Ltd.) was added thereto, and the resulting mixture was stirred at room temperature for 2 hours. After the reaction, the mixture was concentrated using a rotary evaporator. By recrystallization with water, 7.2 g of pure 3-hydroxyadipic acid was obtained. Yield: 95%.

$^1$H-NMR (400 MHz, CD$_3$OD): δ1.70 (m, 1H), δ1.83 (m, 1H), δ2.42 (m, 4H), δ4.01 (m, 1H).

To 7.2 g (0.044 mol) of the pure 3-hydroxyadipic acid obtained, 0.1 L of ultrapure water was added, and 0.01 L of 1 mol/L sulfuric acid was further added thereto, followed by stirring the resulting mixture at 100° C. for 2 hours. After the reaction, the mixture was concentrated using a rotary evaporator. By separation purification by silica gel column chromatography (chloroform:methanol=10:1), 5.8 g of pure 3-hydroxyadipic acid-3,6-lactone was obtained. Yield: 90%.

$^1$H-NMR (400 MHz, D$_2$O): δ2.03 (m, 1H), δ2.04-2.90 (m, 5H), δ5.00 (m, 1H).

Reference Example 4 Preparation of α-Hydromuconic Acid Dimethyl Ester (I-3) and α-Hydromuconic Acid Monomethyl Ester (I-4)

The α-hydromuconic acid dimethyl ester and the α-hydromuconic acid monomethyl ester used in the present invention were prepared by chemical synthesis.

To 5.0 g (0.035 mol) of the α-hydromuconic acid obtained in Reference Example 1, 0.1 L of methanol (manufactured by Kokusan Chemical Co., Ltd.) was added to dissolve the α-hydromuconic acid completely. To the resulting solution, 0.5 g of 98% sulfuric acid (manufactured by Wako Pure Chemical Industries, Ltd.) was added with stirring, and the resulting mixture was stirred at room temperature for 5 hours. After the reaction, methanol was removed by distillation using a rotary evaporator, and an extraction operation was carried out with ethyl acetate (manufactured by Wako Pure Chemical Industries, Ltd.). After the reaction, ethyl acetate was removed by distillation using a rotary evaporator, and separation purification by silica gel column chromatography (hexane:ethyl acetate=10:1) was carried out to obtain 2.8 g of pure α-hydromuconic acid dimethyl ester and 1.7 g of α-hydromuconic acid monomethyl ester.

α-Hydromuconic Acid Dimethyl Ester (I-3)

$^1$H-NMR (400 MHz, CDCl$_3$): δ2.46-2.57 (m, 4H), δ3.69 (s, 3H), δ3.72 (s, 3H), δ5.86 (m, 1H), δ6.91-7.02 (m, 1H)

α-Hydromuconic Acid Monomethyl Ester (I-4)

$^1$H-NMR (400 MHz, CDCl$_3$): δ2.54 (m, 4H), δ3.73 (s, 311), δ5.88 (m, 1H), δ6.91-7.00 (m, 1H).

Reference Example 5 Preparation of 3-Hydroxyadipic Acid Methyl Ester-3,6-Lactone (II-2)

The 3-hydroxyadipic acid methyl ester-3,6-lactone used in the present invention was prepared by chemical synthesis.

To 3.0 g (0.021 mol) of the 3-hydroxyadipic acid-3,6-lactone obtained in Reference Example 3, 0.1 L of methanol (manufactured by Kokusan Chemical Co., Ltd.) was added to dissolve the 3-hydroxyadipic acid-3,6-lactone completely. To the resulting solution, 0.5 g of 98% sulfuric acid (manufactured by Wako Pure Chemical Industries, Ltd.) was added with stirring, and the resulting mixture was stirred at room temperature for 5 hours. After the reaction, methanol was removed by distillation using a rotary evaporator, and an extraction operation was carried out with ethyl acetate (manufactured by Wako Pure Chemical Industries, Ltd.). Subsequently, ethyl acetate was removed by distillation using a rotary evaporator, and separation purification by silica gel column chromatography (hexane:ethyl acetate=10:1) was carried out to obtain 2.6 g of pure 3-hydroxyadipic acid methyl ester-3,6-lactone.

$^1$H-NMR (400 MHz, CDCl$_3$): δ1.93-1.98 (m, 1H), δ2.43-2.84 (m, 5H), δ3.70 (s, 3H), δ4.88 (m, 1H).

Example 1 Production of ε-Caprolactam Using α-Hydromuconic Acid (I-1)

(Condition 1)

In a stainless-steel autoclave with a capacity of 0.2 L (manufactured by Taiatsu Techno Corporation), 1.0 g of the α-hydromuconic acid synthesized in Reference Example 1, 0.1 L of dioxane (manufactured by Wako Pure Chemical Industries, Ltd.), and 0.05 g of γ-alumina supporting 5% by weight of palladium (Pd/γAl$_2$O$_3$, manufactured by Alfa aser) were placed. Subsequently, ammonia gas was introduced into the autoclave such that the internal pressure of the autoclave became 0.35 MPa (gauge pressure), followed by stirring the mixture at 1000 rpm for 30 minutes at room temperature. Subsequently, while the stirring was continued, hydrogen was introduced into the autoclave such that the internal pressure of the autoclave was adjusted to 1.35 MPa (gauge pressure) in terms of the hydrogen partial pressure (total pressure (gauge pressure): 1.7 MPa). Subsequently, the inside of the autoclave was heated at a temperature of 250° C. for 3 hours. After the reaction, the autoclave was allowed to cool to room temperature, and the gas in the autoclave was released to allow the pressure to decrease to normal pressure. The reaction solution was then recovered. The reaction solution was analyzed by gas chromatography, and a solid obtained by concentrating the reaction solution using a rotary evaporator (Tokyo Rikakikai Co., Ltd.) was analyzed by high-performance liquid chromatography (HPLC) and $^1$H-NMR (400 MHz, manufactured by JEOL Ltd.). The results are shown in Table 1. The quantitative analysis of ε-caprolactam was carried out by high-performance liquid chromatography (HPLC). The quantitative analysis of by-products was carried out by gas chromatography. The quantitative analysis of adipamide was carried out by $^1$H-NMR.

Quantitative Analysis of ε-Caprolactam by High-performance Liquid Chromatography HPLC: Prominence (manufactured by Shimadzu Corporation)

Column: Synergi hydro-RP (manufactured by Phenomenex); length, 250 mm; inner diameter, 4.60 mm; particle size, 4 μm Mobile phase: 0.1% aqueous phosphoric acid solution/acetonitrile=85/15

Flow rate: 1.0 mL/minute

Detector: UV (210 nm)

Column temperature: 40° C.

Quantitative Analysis of by-Products by Gas Chromatography

GCMS: GCMS-QP2010 Ultra (manufactured by Shimadzu Corporation)

Column: DB-5; length, 30 m; inner diameter, 0.25 mm; film thickness, 1.00 μm (manufactured by Agilent Technologies)

Carrier gas: helium; constant linear velocity (39.0 cm/second)

Split ratio: 10

Vaporizing chamber: 280° C.

Column oven temperature: 100° C. (4 minutes)→(10° C./minute)→320° C. (11 minutes)

Interface temperature: 280° C.

Examples 2 to 6 Production of ε-Caprolactam (Condition 1)

Production of ε-caprolactam was carried out by the same method as in Example 1 except that the 3-hydroxyadipic acid synthesized in Reference Example 2 (I-2, Example 2), the 3-hydroxyadipic acid-3,6-lactone synthesized in Reference Example 3 (II-1, Example 3), the α-hydromuconic acid dimethyl ester synthesized in Reference Example 4 (I-3, Example 4), the α-hydromuconic acid monomethyl ester synthesized in Reference Example 4 (I-4, Example 5), or the 3-hydroxyadipic acid methyl ester-3,6-lactone synthesized in Reference Example 5 (II-2, Example 6) was used as a material instead of α-hydromuconic acid (I-1). The results are shown in Table 1.

TABLE 1

| | Material | Material conversion rate (%) | ε-Caprolactam yield (%) | Adipamide yield (%) | Hexamethyleneimine yield (%) | Hexanamide etc. yield (%) | Mole balance (%) |
|---|---|---|---|---|---|---|---|
| Example 1 | α-Hydromuconic acid | 100 | 45 | 50 | 5 | Undetectable | 100 |
| Example 2 | 3-Hydroxyadipic acid | 100 | 45 | 45 | 5 | Undetectable | 95 |
| Example 3 | 3-Hydroxyadipic acid-3,6-lactone | 100 | 42 | 45 | 3 | Undetectable | 90 |
| Example 4 | α-Hydromuconic acid dimethyl ester | 100 | 30 | 63 | 2 | Undetectable | 95 |
| Example 5 | α-Hydromuconic acid monomethyl ester | 100 | 38 | 56 | 2 | Undetectable | 96 |
| Example 6 | 3-Hydroxyadipic acid methyl ester-3,6-lactone | 100 | 43 | 43 | 1 | Undetectable | 87 |
| Comparative Example 1 (Patent Document 2, Table 5A Entry 2) | trans-trans Muconic acid | Unknown | 59 | Undetectable | 15 | Detected | 74 |

Comparative Example 1

As Comparative Example 1, results described in Patent Document 2, wherein trans-trans muconic acid (manufactured by Tokyo Chemical Industry Co., Ltd.) was used as a material dicarboxylic acid under the same conditions (in terms of the pressure, temperature, time, catalyst, solvent, and concentration) as in Examples 1 to 6, are also shown in Table 1.

Examples 7 to 12 Production of ε-Caprolactam (Condition 2)

Production of ε-caprolactam was carried out under the same conditions as in Examples 1 to 6 except that α-hydromuconic acid (I-1, Example 7), 3-hydroxyadipic acid (I-2, Example 8), 3-hydroxyadipic acid-3,6-lactone (II-1, Example 9), α-hydromuconic acid dimethyl ester (I-3, Example 10), α-hydromuconic acid monomethyl ester (I-4, Example 11), or 3-hydroxyadipic acid methyl ester-3,6-lactone (II-2, Example 12) was used as a material; the internal pressure of the ammonia gas added in the autoclave was changed to 0.18 MPa (gauge pressure); and the internal pressure of the hydrogen added in the autoclave was changed to 0.72 MPa (gauge pressure) in terms of the hydrogen partial pressure (total pressure (gauge pressure), 0.90 MPa). The results are shown in Table 2.

TABLE 2

| | Material | Material conversion rate (%) | ε-Caprolactam yield (%) | Adipamide yield (%) | Hexamethyleneimine yield (%) | Hexanamide etc. yield (%) | Mole balance (%) |
|---|---|---|---|---|---|---|---|
| Example 7 | α-Hydromuconic acid | 100 | 30 | 66 | 1 | Undetectable | 97 |
| Example 8 | 3-Hydroxyadipic acid | 100 | 25 | 70 | 1 | Undetectable | 96 |
| Example 9 | 3-Hydroxyadipic acid-3,6-lactone | 100 | 18 | 70 | 1 | Undetectable | 89 |
| Example 10 | α-Hydromuconic acid dimethyl ester | 100 | 15 | 80 | Undetectable | Undetectable | 95 |
| Example 11 | α-Hydromuconic acid monomethyl ester | 100 | 30 | 66 | Undetectable | Undetectable | 96 |
| Example 12 | 3-Hydroxyadipic acid methyl ester-3,6-lactone | 100 | 39 | 53 | Undetectable | Undetectable | 92 |

As shown in Table 1, in the case where the trans-trans muconic acid of Comparative Example 1 was used as a material, hexamethyleneimine, which is a reduced product of ε-caprolactam, was produced in a yield of 15%, and production of hexanamide was also found. Further, due to a mole balance of as low as 74%, production of a large amount of unidentified by-products was also found. It is assumed that a laborious separation purification operation may be necessary for obtaining ε-caprolactam.

On the other hand, in Examples 1 to 6, hexamethyleneimine was the only by-product, and its amount yielded was small. Although production of adipamide occurred in a yield of about 45%, it is a reaction intermediate, and can be converted to ε-caprolactam, which is the compound of interest, by subjecting it to a reaction under the same conditions. That is, when necessary, adipamide may be recovered by separation purification, and may then be recycled as a material, to maximize the yield of ε-caprolactam, which is the compound of interest.

In Example 7 to 12, which were carried out under reaction conditions where the partial pressures of ammonia and hydrogen were decreased for providing practical conditions, production of by-products could be suppressed, and adipamide, which can be recycled, as well as ε-caprolactam, which is the compound of interest, could be obtained.

As described above, it was shown that, by using a compound represented by General Formula (I) or (II), and reacting it with hydrogen and ammonia, production of by-products can be suppressed, and ε-caprolactam can be highly selectively obtained.

The invention claimed is:

1. A method for producing ε-caprolactam, comprising the step of reacting a compound represented by General Formula (I) or (II):

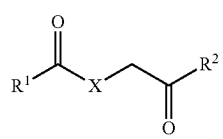
(I)

-continued

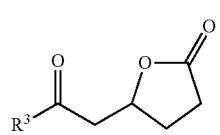
(II)

wherein $R^1$, $R^2$, and $R^3$ each independently represent $OR^4$ or $NR^5R^6$; each $R^4$ independently represents H or $C_1$-$C_5$ alkyl; each $R^5$ independently represents H or $C_1$-$C_5$ alkyl; and X represents —CH(OH)CH$_2$CH$_2$—, CH$_2$CH(OH)CH$_2$—, —CH=CHCH$_2$—, or —CH$_2$CH=CH—, or a salt thereof with hydrogen and ammonia.

2. The method according to claim 1, wherein the compound represented by General Formula (I) or (II) is α-hydromuconic acid, 3-hydroxyadipic acid, or 3-hydroxyadipic acid-3,6-lactone, or an ester thereof.

3. The method according to claim 2, wherein the compound represented by General Formula (I) or (II) is α-hydromuconic acid or an ester thereof.

4. The method according to claim 2, wherein the compound represented by General Formula (I) or (II) is 3-hydroxyadipic acid or an ester thereof.

5. The method according to claim 2, wherein the compound represented by General Formula (I) or (II) is 3-hydroxyadipic acid-3,6-lactone or an ester thereof.

6. The method according to claim 1, wherein said step is carried out in the presence of a catalyst.

7. The method according to claim 6, wherein said catalyst is at least one selected from the group consisting of palladium, platinum, gold, copper, ruthenium, rhodium, cobalt, rhenium, and nickel.

8. The method according to claim 7, wherein said catalyst is at least one selected from the group consisting of palladium, platinum, gold, ruthenium, rhodium, cobalt, rhenium, and nickel.

9. The method according to claim 8, wherein said catalyst is palladium.

10. The method according to claim 1, wherein the hydrogen pressure at the beginning of the reaction in said step is 0.5 MPa to 10 MPa at normal temperature in terms of the gauge pressure.

11. The method according to claim 2, wherein said step is carried out in the presence of a catalyst.

12. The method according to claim 3, wherein said step is carried out in the presence of a catalyst.

13. The method according to claim 4, wherein said step is carried out in the presence of a catalyst.

14. The method according to claim 5, wherein said step is carried out in the presence of a catalyst.

* * * * *